United States Patent [19]

Dinarello

[11] 4,434,237

[45] Feb. 28, 1984

[54] HUMAN LEUKOCYTIC PYROGEN TEST FOR THE DETECTION OF EXOGENOUS FEVER-PRODUCING SUBSTANCES

[76] Inventor: Charles A. Dinarello, 133 Mt. Vernon St., Boston, Mass. 02108

[21] Appl. No.: 363,839

[22] Filed: Mar. 31, 1982

[51] Int. Cl.$^3$ .............................................. G01N 33/56
[52] U.S. Cl. ................................... 436/542; 436/543; 436/545; 436/63; 436/86; 436/804; 436/811; 436/815; 435/2; 435/29; 435/68; 424/1.1
[58] Field of Search .................... 424/1.5, 1.1, 177; 23/230 B; 436/502, 1, 63, 86, 543, 542, 545, 804, 811, 815; 435/2, 31, 2, 29, 41, 68, 244

[56] References Cited

U.S. PATENT DOCUMENTS

| | | | |
|---|---|---|---|
| 3,944,391 | 3/1976 | Harris et al. | 23/230 B |
| 4,038,029 | 7/1977 | Teller et al. | 23/230 B |
| 4,093,381 | 6/1978 | Harris et al. | 356/51 |

OTHER PUBLICATIONS

Dinarello, C. A., International Symposium on Fever (1980) Fever, pp. 1-9.
C. A. Dinarello et al., Clin. Res., vol. 28, 367A, (1980) Human Blood Lymphocytes Produce an Endogenous Pyrogen Producing Factor.
C. A. Dinarello et al., Proc. Natl. Acad. Sci. USA, vol. 74, 4624–4627 (1977), Human Leukocytic Pyrogen: Purification and Development of a Radioimmunoassay.
M. Perlow et al., The Journal of Infectious Diseases, vol. 132, (1975), A Primate Model for the Study of Human Fever.
C. A. Dinarello et al., Cancer Chemotherapy Reports, vol. 57 (1973) 393–398, Pyrogenic Properties of Bleomycin (NSC-125066).
C. A. Dinarello et al., Inflammation, vol. 2, 179–189, (1977) Partial Purification of Human Leukocytic Pyrogen.
C. A. Dinarello et al., The Journal of Experimental Medicine, vol. 139, 1369–1381, (1974), Demonstration and Characterization of Two Distinct Human Leukocytic Pyrogens.
C. A. Dinarello, J. Exp. Med., The Rockefeller University Press, vol. 153, 1215–1224, (1981).
J. Experimental Medicine, vol. 140 (1974) pp. 954–965 Bodel, P.
J. Infectious Diseases, vol. 138 (1978) pp. 760–767, Dinarello, C. A. et al.
Federation Proceedings, vol. 38 (1979) pp. 52–56, Dinarello, C. A.
New England Journal of Medicine, vol. 298 (1978) pp. 607–612, (Bleich, H. L. et al).
J. Clinical Investigation, vol. 60 (1977) pp. 465–476, Dinarello, C. A. et al.
Pharmaceutical Journal, vol. 224 (1980) pp. 259–270, Thomas, W. H. et al.

*Primary Examiner*—Benjamin R. Padgett
*Assistant Examiner*—M. Moskowitz
*Attorney, Agent, or Firm*—Oblon, Fisher, Spivak, McClelland & Maier

[57] ABSTRACT

A method for determining the pyrogenicity of a substance, comprising the step of incubating said substance in the presence of a cell mixture for at least 46 hours at 35° to 39° C., wherein the cell mixture comprises human lymphocytes and human monocytes with a cell ratio of lymphocytes to monocytes of at least 2:1 and a composition with respect to the total of all cells present comprising at least 15% monocytes and no more than 10% granulocytes and wherein the cells have a contact ratio of from 0.0 to 0.75.

48 Claims, No Drawings

HUMAN LEUKOCYTIC PYROGEN TEST FOR THE DETECTION OF EXOGENOUS FEVER-PRODUCING SUBSTANCES

BACKGROUND OF THE INVENTION

1. Field of the Invention

The present invention relates to a test for the detection of exogenous fever-producing substances in which an incubation of the substance with human monocytes and lymphocytes produces human leukocytic pyrogen.

2. Description of the Prior Art

The recent development of the ability to manipulate genes has resulted in a new source of pharmaceutical substances. Genes for desirable, naturally occurring drugs, such as interferon, insulin, and human growth hormone, have been removed from normal human cells and inserted into bacterial cells, which may then be used as biological factories of these important biochemical substances. It is anticipated that more and more pharmaceuticals will become available in this fashion, as techniques of genetic manipulation continue to improve.

Unfortunately, pharmaceuticals derived from bacteria are often contaminated with minute quantities of material that may cause undesirable effects when administered parenterally to humans. One such undesirable effect is the production of fever. Studies of fever in response to injections go back to the 19th century, when the lipopolysaccharide of gram-negative organisms (bacterial endotoxin) was recognized as a fever-producing agent (a pyrogen). This is only one of many substances, most of microbial origin, that cause fever when injected into humans. Although other animals may also demonstrate fever when injected with the same substances, there is considerable variation from species to species, and the production of fever by a substance in one species may not mean that fever will be produced in another. Thus tests for pyrogenicity of materials intended for human parenteral administration may be misleading if based on the reaction of another species.

The only standard test currently available for the detection of the pyrogenicity of materials are the rabbit pyrogen test (USP) and the Limulus amebocyte lysate test. As these tests are based on the response of a non-human animal or cells derived from a non-human animal, their reliability has often been questioned, for example, in "Nonspecificity of the Limulus amebocyte lysate test: Positive reactions with polynucleotides and proteins," Elin et al., J. Inf. Dis., 128:349–352 (1973).

Because of the shortcomings of animal-based tests, a test more closely corresponding to human fever response is needed, one which will mimic in vitro the fever response that exogenous pyrogens induce when they are administered parenterally to humans. Investigations into the pathogenesis of fever production by pyrogens has established that pyrogens do not cause fever by a direct effect on the thermoregulatory center but rather by an indirect mechanism. This mechanism involves the stimulation of leukocytes by exogenously injected pyrogens to synthesize and release an endogenous pyrogen, which is also called leukocytic pyrogen (LP). LP is a polypeptide of 15,000 daltons which is produced by phagocytic leukocytes, primarily the mononuclear phagocytes (monocytes). Evidence that LP mediates fever is drawn from 30 years of research into the pathogensis of fever. Following the injection of exogenous pyrogens obtained from either microbial or non-microbial sources, LP appears in the circulation of experimental animals. In addition, incubating exogenous pyrogens with phagocytic leukocytes in vitro induces the production and release of LP into the supernatant medium. Human leukocytes which have been stimulated by exogenous pyrogens in vitro often release LP into the culture medium after several hours of incubation. When the medium is injected into human subjects, there is rapid onset of fever. An assay for the presence of human LP can also be carried out in rabbits and in mice, where it produces a similar febrile response. The rapid onset of fever is characteristic of LP from all species studied and represents the ability of this molecule to directly affect the thermoregulatory center and initiate fever.

The critical role of LP in the pathogenesis of fever is underscored by the correlation that exogenous pyrogens which produce fever in humans also stimulate human leukocytes to release LP in vitro. This has been shown for a variety of exogenous pyrogens including several microbial pyrogens, poly I:C, bleomycin, colchicine, bacterial endotoxin, etiocholanolone, and synthetic adjuvants [reviewed in Dinarello and Wolff, Seminars in Inf. Dis., 2:173–192 (1979)]. Of particular interest are studies of etiocholanolone, which is nonpyrogenic for the monkey, rabbit, dog, cat, guinea pig, rat or mouse but highly pyrogenic when injected into humans. When incubated with leukocytes, etiocholanolone induces LP production from only human cells. Additionally, the synthetic adjuvant muramyl dipeptide and several of its analogs produce fever in humans and cause LP production from human monocytes in vitro; moreover, side-chain substitution of these adjuvants associated with decreased ability to stimulate LP production in vitro is also less pyrogenic for humans. Therefore, the ability of a substance to induce LP production in vitro from human leukocytes seems to correlate with its ability to cause fever in the intact host.

There are, however, no established procedures for the certain and unequivocal detection of exogenous pyrogens using a test based on induction of LP synthesis. Although many investigations of the pathogenesis of fever production have involved measurement of LP production by pyrogens during in vitro incubations with leukocytes, not all pyrogenic substances induce LP production during a normal period of incubation, which is generally 24 hours. Although longer incubations may be carried out in an attempt to induce LP production, such longer incubations using these prior art procedures invariably lead to autostimulation, which produces LP even in the absence of any added material. Thus, prior art methods for the detection of LP production lead to false negatives if the time of incubation is about 24 hours or less and false positives if the time of incubation is much more than 24 hours.

Thus, at the time the present invention was made, there was still a need for an accurate and reliable test for determining which of those substances intended for parenteral administration to humans were either pyrogens themselves or were contaminated with pyrogens.

SUMMARY OF THE INVENTION

Accordingly, it is an object of this invention to provide a test for the detection of exogenous fever-producing substances which mimics in vitro the biochemical processes induced by the parenteral administration of a pyrogen to a human.

It is a further object of this invention to provide a test for the detection of pyrogens which reduces the number of false positive and false negative results associated with current tests for pyrogens which utilized non-human cellular response.

These and other objects of the invention, as will hereinafter become more readily apparent, have been accomplished by providing a method for determining the pyrogenicity of a substance, comprising the step of incubating said substance in the presence of a cell mixture for at least 46 hours at 35° to 39° C., wherein said cell mixture comprises human lymphocytes and human monocytes with a cell ratio of lymphocytes to monocytes of at least 2:1 and a composition with respect to the total of all cells present comprising at least 15% monocytes and no more than 10% granulocytes and wherein said cells have a cell contact ratio of from 0 to 0.75.

DESCRIPTION OF THE PREFERRED EMBODIMENTS

The present invention arose with the discovery that, when proper controls were used, incubations of human lymphocyte/monocyte mixtures with suspected pyrogens for about 48 to 168 hours produced human leukocytic pyrogen (LP) without excessive false positives or false negatives. Prior to the present invention, it was known that incubation of a pyrogen with a lymphocyte/monocyte mixture would produce LP. However, it was thought that incubation periods of more than about 36 hours would cause many false positives because of autostimulation, since incubations of 36 or more hours using conditions previously taught often caused production of LP even in the absence of any exogenous substance. Shorter periods of incubation resulted in lower, inconsistent, and undetectable levels of LP production in the presence of known pyrogens. Accordingly, other tests, such as the Limulus amebocyte lysate assay and rabbit pyrogen test (USP), were used for the evaluation of pyrogens. These tests unfortunately suffer from the previously discussed disadvantages associated with tests based on non-human cellular response. The present invention therefore represents a major advance in efforts to identify potentially pyrogenic pharmaceuticals or to identify particular lots of non-pyrogenic pharmaceuticals that are contaminated with trace amounts of highly active pyrogens.

Generally, the invention consists of a method for determining the pyrogenicity of a substance, comprising the step of incubating said substance in the presence of a cell mixture for at least 46 hours at 35° to 39° C. wherein said cell mixture comprises human lymphocytes and human monocytes with a cell ratio of lymphocytes to monocytes of at least 2:1 and a composition with respect to the total of all cells present of at least 15% monocytes and no more than 10% granulocytes and wherein said cells have a cell contact ratio of from 0.0 to 0.75. The essential step of the total method is this incubation, although in order to perform a complete assay, it is naturally necessary to assay the supernatant of the cell culture at the end of the incubation period for the presence of LP. Methods of analysis for LP are currently known, and two such methods will be described in detail in a later section. Any method now known, or discovered in the future, for qualitatively or quantitatively detecting the presence of LP may be used to carry out this final step of the overall method without affecting the invention.

The overall method also includes steps that occur before the inventive step; for example, steps relating to the preparation of the cell mixture. Again, however, the exact nature of these steps is unimportant so long as the cell mixture previously described is obtained. Examples of steps both precedent and subsequent to the essential step of the invention will be given at various locations of this invention disclosure. Such steps, either generally or specifically described, may represent preferred embodiments when taken in combination with the inventive step but are in no way to be considered limitations of the essential nature of the invention, which relates to the incubation step.

The preparation of cell mixtures in anticipation of an analysis for pyrogenicity will generally be the first step of an overall assay. Cell donors should be selected from healthy, well-nourished adults taking normal diets. Preferred are donors with no chronic diseases, such as diabetes, hepatitis, or autoimmune disorders, and no recent illnesses, such as influenza, pharyngitis, or upper respiratory infection (URI). Even more preferred are adults (male or female) inclusively between the ages of 18 and 65 who are taking no chronic (weekly or more often within the previous year) medications such as megavitamins, birth control pills, anti-depressants, narcotics, anti-hypertensives, or anti-anxiety preparations, and are not chronic (monthly or more often within the previous year) psychotomimetic drug users. Most preferred are donors who additionally have had no recent (within 3 days) aspirin, antihistamines, analgesics, or anti-inflammatory drugs. Since cellular response slows with increasing age, sensitivity of the assay may be increased by choosing donors who are no more than 55 years of age, preferably no more than 35 years of age. Serum, used in some of the cell cultures, should be obtained from donors selected using the same criteria as for cell donors with the additional requirement for all levels of preference that the blood type be AB, preferably type D variable.

Cells are obtained from the blood of donors. Since cells are being separated from the blood, clotting must be prevented by use of an anticoagulant at time of blood sampling. Any anticoagulant, such as citrate, may be used, although heparin is preferred. A particularly preferred blood sample would be obtained from a morning, fasting donor by collection of approximately 60 ml of venous blood into a heparinized plastic syringe, at a final heparin concentration of 10 to 100 units/ml, most preferably about 30 units/ml.

The cells of the uncoagulated blood may be separated into fractions using any standard technique. Centrifugation using either a continuous or discontinuous density gradient is a preferred technique. Preferably blood is diluted prior to centrifugation using an aqueous, pyrogen-free diluent containing the same anticoagulent used in collecting the blood sample. Suitable diluents include isotonic (or nearly isotonic) solutions of salts, such as NaCl, or non-toxic organic compounds, such as glucose. The most preferred diluent is pyrogen-free saline (PFS) at or near physiological concentration. Any amount of diluent is acceptable, although dilutions of less than 10:1 are preferred for convenience of handling. A dilution of one part blood to two parts PFS is most preferred. In a preferred centrifugation technique, diluted blood in a centrifuge tube is layered over or underlayered by a concentrated aqueous solution of any nonreactive solute, preferably nonionic, most preferably Ficoll-Hypaque mixture, to form a discontinuous density gradient. The density of the lower layer of the gradient is chosen so that monocytes and lymphocytes collect at the boundary between the upper layer of diluted blood and the lower, high-density layer. The tube containing the cells and gradients is then centrifuged at a spin rate sufficient to cause the cells to settle faster than they would under normal gravity, and spinning continues until cells have collected at the gradient boundary. This time period will vary with rate of revolution and distance from the center of revolution (i.e., with the type of rotor head) as is well understood. Suitable times can be calculated or determined by routine experimentation. For example, a preferred time of an IEC-model swinging-bucket centrifuge using 50 ml conical centrifuge tubes, 30 ml diluted (2:1 with PFS) blood, and 10 ml Ficoll-Hypaque mixture is 40 minutes at 1250 rpm. Centrifugation may be at room temperature or with refrigeration. Crude cell mixtures obtained in this way may be washed with diluent, spun down, resuspended in diluent, and recentrifuged on a gradient to obtain the desired cells further separated from extraneous materials from the original blood sample. Two such additional gradient centrifugation cycles are preferred. Any separation technique, such as that described above, which principally separates monocytes and lymphocytes from other blood components is suitable for use with this invention. Small amounts of additional types of cells may be present, subject to the provisions cited elsewhere in this application.

Once cells are obtained essentially free of noncellular matter, the cells are suspended in a cell culture medium capable of maintaining lymphocytes and monocytes in a viable state. A suitable medium is RPMI 1640. Preferred are liquid media that will allow cells to settle freely under the influence of gravity, for example Minimal Essential Medium (MEM), which contains Earl's Balanced Salt Solution, 2 mM L-glutamine, 100 mg/ml streptomycin, 100 units/ml Penicillin G, and 0.01 M HEPES buffer. In addition, the LAL test (described later) should show less than 50 pg endotoxin/ml medium. Cell concentration is adjusted in the chosen medium to from $1 \times 10^5$ to $2.5 \times 10^7$ total cells milliliter, preferably from $2.5 \times 10^6$ to $1 \times 10^7$ cells/ml, most preferably about $5 \times 10^6$ cells/ml. A Coulter Counter or other cell counter may be used to count the cells in a given volume.

At this point of the procedure it is convenient to determine if the cells meet the distribution requirements previously stated. Any method of differential cell counting involving at least 100 total cells is sufficient. A preferred technique comprises cytocentrifuging a sample of the cell culture in about 1% serum albumin, preferably human, staining the cytocentrifuge preparation with Wright's stain, and performing a differential cell count under coil under oil on 300 cells. If the ratio of lymphocytes to monocytes is less than 2:1, the preparation is discarded and a new donor is selected. The preparation is also discarded if it contains, relative to the total of all cells present, less than 15% monocytes or more than 10% granulocytes. Preferred limits are a lymphocyte/monocyte ratio of at least 7:2, at least 20% monocytes, and no more than 10% granulocytes. Most preferred limits are a lymphocyte/monocyte ratio of about 2:1, about 30% monocytes, and no more than 10% granulocytes.

An essential feature of the practice of this invention is the need to prevent cells from accumulating at high concentrations (clumping) as they settle out of the initial cell suspension. Although the inventor does not wish to be limited by theory, it is believed that clumping of cells is an important factor in causing autostimulation, and thus false positive results. Clumping of cells can be prevented by carrying out the incubation in a container having a geometry that prevents localized accumulation of cells. Accumulation generally occurs at low points on the bottom surface of the container during incubation as the cells settle under the influence of gravity. Accordingly, containers that have a low point surrounded by sloping walls, such as round-bottomed test tubes, are particularly prone to inducing autostimulation. On the other hand, containers with vertical sides and flat bottoms are particularly suited for use in the practice of the present invention. What is a "bottom" or "side" is determined during incubation.

However, it must be pointed out the geometry of the flask or the manner in which it is treated is important only in that uniform contact is achieved between cells. By uniform contact is meant that the cells are distributed randomly and without localized severe clumping across the surface of the container that they are contacting. Since cells tend to settle to the bottom of a container unless they are kept in suspension by agitation of the medium, this surface is generally the bottom of the container. The container bottom may be any convenient geometry, such as steps, wells, or concentric rings having horizontal surfaces, onto which the cells may evenly settle from a uniform suspension. Flat-bottomed containers are simple to make and use and are thereby preferred. The bottom need not have a horizontal surface, however, if provision is made to prevent settling of cells to the low point of the containers under the influence of gravity. For example, minute grooves or a surface coating having adhesive properties may be used to prevent cells from sliding "downhill" from their initial point of contact as the cells settle in the container. It is also possible to reduce the nutrient volume and maintain the cells in contact while fresh nutrient is supplied. In all cases the important variable being controlled by this feature of the invention is the cell contact ratio; i.e., the average amount of surface of a cell that contacts any other cell divided by the average amount of surface area per cell. Although this value has not been measured for the present invention, the most preferred value of the cell contact ratio that which is present when $5 \times 10^6$ total cells are allowed to settle evenly from 1 ml of the medium in which they are suspended onto a horizontal surface having an area of 5 cm$^2$. The cell contact ratio determined in this manner is defined to be one unit contact ratio (UCR) for the purpose of this application. A cell contact ratio of from 0.0 to 0.75 is acceptable, with 0.10 to 3 UCR being preferred, and 0.33 to 2.0 UCR being more preferred. Preferred ranges are subject to the proviso that the upper limit does not exceed a cell contact ratio of 0.75. Expressed differently, there preferably should be at least some contact between an average cell and its neighboring cells, and the amount of contact should be controlled so that deep, multiple layers of cells do not develop. When the cell contact ratio is 0.0 (i.e., the cells are mostly not touching) the average distance between cells should be no more than 10 microns.

The cell cultures are now ready for incubation with a material being tested for pyrogenicity. The cell suspension is added to any conveniently sized, sterile container. The container size depends on the volume of cell suspension used. If a flat-bottomed container is used, it should have from 1 to 25 cm² of flat-bottomed surface per ml of cell culture. More preferred is from 2 to 10 cm²/ml, with about 5 cm²/ml being most preferred. A convenient, and therefore preferred, embodiment uses 5 ml of cell suspension in a 25 cm² sterile glass or plastic flask (e.g., Corning or Falcon). If plastic flasks are used, they should be aged; i.e., placed in storage, until inhibitory plasticizers or residual oxidants no longer interfere with the test. This period should be at least 3 months, and preferably at least 6 months, for 25 cm² Corning or Falcon plastic flasks.

The material to be tested is added to a flask at a concentration proportional to the dose rate at which it would enter the blood stream in a pharmaceutical preparation in which the material was used. The concentration of material per $10^6$ mononuclear cells in the cell suspension may range from 0.1 to 10 times the dose rate expressed in mg/kg. A simple example will illustrate this calculation. If material A will be administered at a rate of 10 mg/kg of blood weight, then from 1 mg ($0.1 \times 10$ mg) to 100 mg ($10 \times 10$ mg) of A would be added per $10^6$ mononuclear cells in the cell suspension. More preferred are amounts from 0.5 to 2 times the mg/kg dose rate per $10^6$ mononuclear cells; most preferred is the exact anticipated dose rate/$10^6$ cells. Naturally, if the anticipated dose rate is unknown, a series of differing concentrations may be run to determine the maximum allowable dose.

Although pyrogenicity may be determined without the use of control samples, such samples are desirable and are essential if the test is being used as a definitive test for pyrogenicity. For example, an antibiotic such as Polymyxin B may be added to one unknown sample to prevent bacterial contaminations; Polymyxin B is preferred since it prevents endotoxic stimulation of human mononuclear cells. The concentration of the antibiotic is adjusted to be within its established effective range. For Polymyxin B the range is 10 to 15 $\mu$g/ml, but 12.5 $\mu$g/ml is preferred. A difference between the Polymyxin B sample and the unknown sample would indicate the presence of a bacterial endotoxin infection of the unknown sample incubation. Other desirable controls include a sample containing cell suspension, unknown, and 2 to 15%, preferably about 5%, heat-inactivated AB serum. The serum sample is included as a precaution in the event that the unknown is more pyrogenic in the presence of serum than in its absence, an occasional occurrence with known pyrogens. Another control would contain both Polymyxin B and serum in addition to unknown. Generally, an additional series of control incubations not containing any of the unknown being tested would also be run. This series would include samples containing cells and each of the other individual components of a test incubation but without the unknown being tested. Also included would be a positive control comprising cells and a known pyrogen. Suitable materials for use in positive controls include viruses, such as influenzal and coxsachie virus; intact gram-positive baceteria, such as *Staphylococcus aureas, S. albus*, pneumococci, *Bacillus subtilis*, and *Listeria monocytogenes;* non-microbial particles, such as colloidal fat, glycogen, silica, and thorium dioxide; extracellular products from gram-positive bacteria, such as various protein antigens; gram-positive cell wall components, such as peptidoglycans containing N-acetylglucosamine and N-acetylmuramic acid; gram-negative organisms and their products, such as lipopolysaccharides (LPS); yeast cells, such as *Candida albicans* and *Saccharomyces cerevisiae;* soluble fungal products; mycobacteria; and spirochetes, such as *Borrelia hermsuu*. A preferred embodiment uses heat-killed *S. albus* cells as its positive control, since the stimulation of LP synthesis in vitro by killed gram-positive organisms has been shown to be dependent on the ratio of bacterial particles to leukocytes in a close-responsive relationship by Atkins et al., Yale J. Biol. Med., 39:297–311 (1967) and Root et al., J. Lab. Chem. Med, 75:679–693 (1970). No matter which pyrogen is selected for use in the positive control, the pyrogen is added at a concentration suitable to elicit a definite and measurable response in the test being used to assay for LP. The actual amount required will depend on which LP assay method is used and on the pyrogenicity of the standard and can be easily determined by routine experimentation if not already known or published. When heat-killed *S. albus* is used, 0.4 to 40 $\mu$l, preferably about 4 $\mu$l, of a standardized *S. albus* cell suspension is added per $10^6$ cells of the cell culture. By standardized cell suspension is meant an optical density at 530 mm of 3.3.

The use of the various controls described above is described more completely in the following sections, particularly in the section relating to analysis of the test results.

Once a series of test incubations and controls has been prepared, the containers are incubated for at least 46 hours, preferably from 46 to 168 hours, and most preferably for about 48 hours, at 35° to 39° C., preferably about 37° C. The suspensions should have access to air, preferably humidified air to prevent excessive evaporation of the culture medium fluid, and most preferably 5% $CO_2$-95% humidified air. The incubation should take place on a flat surface so that there is no tendency for the cell suspension to settle and collect at one end of the flat-bottomed container. If screw-top flasks are used, the caps should be about ½ turn less than tight.

Once incubation is complete, any method of determining LP may be used to complete the test for pyrogenicity. If LP is present in the container to which the unknown was added but is not present in controls to which no unknown was added, then the unknown is inducing the formation of LP from the lymphocyte/monocyte cell suspension and has a high probability of acting as a pyrogen if injected parenterally. Several examples of methods used to assay for the presence of LP in a fluid follow but are not considered to limit the invention.

For the method described below, and probably for most methods by which LP could be detected, the first step after incubation would be separation of the supernatant containing excreted LP from the cells of the cell suspension. Various methods of cell separation, such as filtration and centrifugation, may be used. Centrifugation at 2500×g for 30 minutes is sufficient to form a compact pellet of cells in the bottom of a conical centrifuge tube that will not be disturbed by decantation. The supernatant is poured into another tube, in which it may be stored, and a preservative, such as 0.02% sodium azide, may be added. The supernatant may be stored at 4° C. for at least 6 weeks before it is assayed. Freezing at −70° C. or below may be used for storage periods of up to 1 year or if the sample is to be shipped (on Dry-Ice).

Two assay procedures for determining the presence of LP are described herein. The first of these relies on the ability of human LP to produce a febrile response in an animal. Any animal which demonstrates a febrile response to injection of human LP is satisfactory, although standard laboratory mammals are preferred for their ease of handling. Most preferred are rabbits; although other breeds of rabbits may be used, adult, albino, New Zealand-derived virgin females of approximately 3 kg ($\pm$500 g) weight are recommended since these are the rabbits used in establishing this procedure. It is recommended that hay (dried grass) be included in the rabbits' diet to promote the formation of a hard fecal pellet, which reduces the chance that rectal probes will be displaced during the assay. Rabbits are housed in individual cages at 68° F. and trained in metal restrainers prior to use.

The rabbits are trained over 3 consecutive days before they are given any injections of supernatants from the lymphocyte-monocyte cell cultures. On day 1, the rabbits are placed in the restrainer for 4 hours. On day 2, they are placed in the restrainer for 6 hours. On day 3, the rabbits are placed in the restrainer with a rectal temperature probe for 4 hours. Also on day 3, 5 ml of pyrogen-free saline is injected by intravenous bolus, and the temperature of the rabbit is recorded. On day 4, the rabbits are given standardized injections (i.v.) of semipurified, standardized human LP stabilized in 0.1% heatinactivated rabbit serum. The terms "standardized", "semi-purified", "stabilized", and "heat-inactivated" are defined in the notes following the most preferred embodiment, which is given later in this application. The rectal temperatures of the rabbits are recorded at the time of injection. This injection is repeated on days 5 and 6. Since the standardized LP preparation is stable for several months, the responses of various rabbits can be compared in order that rabbits showing low response, high response, or unstable base-line temperatures may be rejected. Rabbits which on three standardization tests demonstrate a mean peak fever of less than 0.5° C. within 60 minutes following i.v. bolus injection are rejected. Likewise, rabbits which on three standardization tests exceed a mean of 1.0° C. peak fever over base-line are also rejected. The base line temperature is determined by the temperature immediately before and after the injection. Temperatures are recorded at intervals of 5 to 10 minutes while the rabbit is in the restrainer. If the temperatures before and after the injection are not the same, then the two readings preceding the injection are used. If these temperatures are not the same, then the mean of the two preceding and the reading following the injection is calculated and used as the base-line temperature.

Peak fever is determined to be the highest recording above the base line that occurs within 56 minutes following injection. Peak readings occurring at 64 minutes or later invalidate the test, as this is not typical LP fever.

Peak fever may be used to quantitate the amount of LP in the supernatant. Three rabbits are used to assay a sample, and the mean is calculated. A mean fever of less than 0.3° C. is not considered significant. A mean peak above 0.3° C. is considered evidence that the cells were stimulated to produce LP in vitro.

In addition to testing for pyrogenicity of the materials, it is also possible to use this same test to test for anti-pyretic properties. In order to carry out this test, the same amount of material that is used for a test for pyrogenicity is added to the standardized human LP preparation, incubated for 1 hour at 37° C., and injected into three rabbits. If the rabbits have a mean peak fever between 0.5 and 1.0° C., no interference is present. If the mean peak fever of the rabbits is less than 0.5° C., the material has anti-pyretic activity.

In carrying out the injections of supernatants from incubations of both unknowns and controls, the following procedure is preferred. Proper amounts of material for injection are calculated from the concentration of monocytes present in the cell incubation. This is easily determined from the percentage of monocytes present in the donor cell preparation and the total cell count of the cell culture. Each 3 kg rabbit is injected with the supernatant derived from $1.5 \times 10^5$ to $1.5 \times 10^7$ monocytes, preferably from $3 \times 10^6$ monocytes (about $1 \times 10^6$/kg). The cell control, which consists of a cell culture medium and additional medium added so that the volume is the same as that of the other samples, is injected in triplicate, as is a serum control which contains cells and heat-inactivated AB serum. These controls should not yield mean fevers of 0.3° C. or greater. If they do, the entire assay must be rejected since this indicates autostimulation. The positive control, for example, a Staphylococcal control is likewise injected in triplicate. Peak fevers for this positive control should have a mean of 0.6 to 0.9° C. Higher mean peaks do not invalidate the assay, but rather represent variability of the assay. However, a mean peak fever of less than 0.5° C. for the positive control indicates poor cell response to a standard stimulus and invalidates this particular assay. If the sample is also being tested for antipyretic activity, the positive control/unknown incubation supernatant is also injected in triplicate. Those agents having anti-pyretic activity will suppress the febrile response. Mean peak fever of less than that observed following the injection of the positive control by 50% indicates significant suppression and anti-pyretic activity. Peak fevers higher than that for the positive control may indicate that the unknown material is an exogenous pyrogen. This pyrogenicity would be confirmed by the unknown samples described below. If the unknown samples in the absence of the positive control material do not cause a febrile response and therefore do not contain significant LP, then facilitation (synergism) has occurred in this positive control/unknown sample. This may or may not have clinical significance.

Once the various control samples for interference of dialyzable supernatants have been properly carried out as described above, the supernatants from incubations with unknowns (suspected pyrogens or other materials being tested) can be injected in triplicate at the rate of the supernatant from $3 \times 10^6$ monocytes per 3 kg rabbit. Mean peak fever 0.3° C. or greater indicates a positive response and indicates that a contaminating pyrogenic agent is present or that the material being tested is capable of inducing LP; i.e., is pyrogenic. Supernatants from cultures containing heat-inactivated AB serum and/or an antibiotic are likewise injected and the results calculated in the same manner. Reduced febrile response in the antibiotic-containing samples may be an indication that a positive response in the unknown sample is due to endotoxin (LPS) contamination if Polymyxin B is used as the antibiotic. Polymyxin B has the ability to prevent endotoxin stimulation of human mononuclear cells.

If the rabbit assay indicates the pesence of a nondialyzable interfering substance, immobilized anti-LP may be used to prevent this interference from occurring. The preparation and characteristics of this antibody are described in "The production of antibody against human leukocytic pyrogen," Dinarello et al., J. Clin. Invest., 60:465–472 (1977).

Sephrose-4B anti-LP (1.0 ml) is placed in a nylon wool-plugged, Pasteur pipette (or a similar pyrogen-free column) rinsed with 5 ml of phosphate-buffered saline (PBS) (pH 7.4; 0.15 M NaCl, 0.005 M Na$_2$HPO$_4$, 0.007 M NaH$_2$PO$_4$). Supernatant (5 ml) is placed over the immunoadsorbent and eluted at a rate of 1 ml/min at room temperature. The immunoadsorbent is then washed with 5 ml of PBS. This is followed by 5 ml of citric acid buffer, pH 3.0, which is eluded at 1 ml/min and neutralized to pH 7.0 to 7.5 with 0.1 N NaOH. The eluent obtained in this matter is then injected into rabbits. Each rabbit-receives one-third of the final volume.

If a substance being tested gives no significant fever (a mean fever of less than 0.3° C.), the incubations are repeated on cells obtained from two or more different donors because of possible donor variability. If the cell incubation responses of all three donors are negative, then the substance being tested passes the LP-assay test and is highly unlikely to produce fever in humans. If the cell incubation response for one of the three donors is positive (mean peak fever greater than 0.3° C.), a fourth donor is used. If incubations of the substances being tested with the cells from the fourth donor produces LP, then the substance is considered to be pyrogenic and should not be used in a pharmaceutical preparation. If this fourth incubation is negative, the substance is retested in a fifth and sixth trial. If no LP is produced during the fifth and sixth trails (mean peak fevers of less than 0.3° C.), then the substance is considered to be non-pyrogenic since only one of six assays produced a pyrogenic response.

In addition to the rabbit-based assay described above, it is also possible to assay for LP in supernatant media using a radioimmunoassay procedure. Such a procedure would require an antiserum against human LP and radiolabeled-LP. Both of these materials are available and are described in, for example, Dinarello et al., J. Clin. Invest., 60:465–472 (1977). Radioimmunoassay (RIA) is a well-established clinical procedure which does not need to be described in detail at this time. For particulars, reference is made to Chard, "An Introduction to Radioimmunoassay and Related Techniques," North-Holland Publishing Company, 1978, which is herein incorporated by reference. Any of the many variations of RIA can be used, such as homogeneous phase RIA, heterogeneous or solid phase RIA, single antibody methods or double antibody methods, and direct (forward) or reverse sandwich assays. Particularly preferred are solid phase systems wherein the antibody (IgG or IgM) is covalently coupled to an insoluble support so that both the antibody and the bound complex after incubation can be readily separated from the soluble free fraction. A wide variety of solid phase supports have been described, which include particles of dextran, cellulose, continuous surfaces such as polystyrene or polypropylene discs, walls of plastic tubes, glass discs, glass particles, and the like. Particulate solid phases are widely used for a variety of assays and may be used with an assay containing the incubation step of the present invention. Antibodies are attached to the particles by any of a several of techniques designed to yield a non-reversible covalent or non-covalent link between protein and particle; for example, directly or by cyanogen bromide activation. Another alternative is the use of antibodies entrapped in the interstices of a polyacrylamide gel or bound to magnetic particles. An assay tube is set up containing either sample or standard, along with the tracer and an appropriate amount of solid phase bound antibody, plus a detergent to prevent aggregation of the particles and non-specific absorption of the tracer. After an incubation period during which the tubes are continuously mixed, the solid phase is sedimented by centrifugation; the supernatant is removed, and the solid phase is subjected to two or more washes with buffer in order to remove free tracer trapped within and between the particles. The counts on the solid phase (bound fraction) are then measured. Immunoradiometric assays, as described in Chards at page 423, can also be used. When a second antibody radioimmunoassay system is used, the second antibody may be IgM or may be IgG.

Another immunoassay technique useful with the antibodies of the present invention is enzyme immunoassay. This technique is also well known to the art and reference is made to Schuurs and VanWeeman, Clinica Chimica Acta, 81:1–40 (1977), which is herein incorporated by reference. In this technique, enzymes are applied as labels on antigen or antibodies for identification and localization of the immunoreactants. Any method in which the extent of binding of enzyme-labeled antigen or enzyme-labeled antibody to its immunoreactant is measured may be used in practicing the assay for LP. Enzyme immunoassays can be classified as homogeneous or heterogeneous, depending on whether or not the labeled reagent has different enzymatic activity when it becomes bound to specific counterparts in the immuno-reaction. Enzymes used in homogeneous assays have different properties when they become bound and therefore do not require physical separation of the reactants into two fractions. The variety of enzymes used, methods of linking enzymes to the immunological components, and purification of the conjugates, as well as various assay principles and methods, are well described in the aforementioned Schuurs and VanWeemen article. Of course, any enzyme immunoassay which has employed antibodies in the pase can be used in carrying out the assay for LP.

Another immunoassay method useful with the present invention is the latex agglutination method. In this method, latex particles are coated with antigen derived from LP (generally either intact LP or a fragment) and incubated with IgM antibodies. Inhibition of agglutination will occur when a sample of supernatant fluid containing LP is incubated with this mixture. The inhibition of agglutination can either be followed with a counter or by recently developed infrared absorption techniques. An alternative is to coat the latex particles with anti-LP antibodies. Incubation of these coated particles with physiological fluid containing LP will cause agglutination. Instead of latex particles, animal cells such as red blood cells can of course be used. In this case, the technique becomes a variation of the well-known hemagglutination technique used with IgG antibodies and red blood cells.

Other useful immunoassay techniques are those employing other labeling techniques such as:

fluorescent dyes, Aalbeses, Clin. Chim. Acta, 48:109–111 (1973);

electron-dense compounds (such as ferritin), Singer et al, J. Biophys. Biochem. Cyto., 9:519–537 (1961);

protein-bacteriophage conjugates, Haimovich et al., Biochim. Biophys. Acta, 207:115–124 (1970); or stable free radicals, Bastiani et al., Am. J. Med. Technol., 39:211–216 (1973).

As can be seen from the foregoing general disclosure, many methods of assaying for pyrogens are possible which would utilize the essential incubation step of the present invention. Since the essence of the invention is to provide an incubation procedure that produces LP in the presence of pyrogens with a minimum of false positive and false negative results, the incubation step of the invention can be used in any assay which involves measuring the production of LP, whether as part of an overall procedure used to test for the pyrogenicity of prospective pharmaceuticals or not. However, such a use is believed to be the most important use of this incubation step, and a detailed procedure of the most preferred embodiment of this use is given in the following outline:

Human Leukocytic Pyrogen Test for the Detection of Exogenous Pyrogens in Pharmaceuticals Intended for Parenteral Use in Humans 1. Selection of Donors (cells)

(a) Male or female (ages 18 to 65), well-nourished, taking normal diets. No chronic medications; no megavitamin doses; no recent (36 hours) aspirin, antihistamines, analgesics, or anti-inflammatory drugs; no birth control pills, anti-depressants, narcotics, anti-hypertensives, or anti-anxiety preparations. No chronic psychotomimetic use.

(b) No chronic diseases (diabetes, autoimmune, hepatitis, or others).

(c) No recent illness (influenza, pharyngitis, URI, or other infectious or inflammatory diseases). A 14-day resolution period, without signs or symptoms, should be ascertained by a licensed physician.

2. Selection of Donors (serum)

(a) Male or female with same requirements in 1a, 1b and 1c.

(b) AB blood type, type D variable.

3. Preparation of Mononuclear Cells (a) AM fasting, collect into 60 ml heparinized plastic syringes, venous blood (final heparin concentration, 30 units/ml).

(b) Dilute one part heparinized blood with 2 parts heparinized, pyrogen-free saline (PFS). Place 30 ml of dilute blood into 50 ml conical polypropylene tubes. Underlayer 10 ml of Ficoll-Hypaque mixture with 14 g. needle. Spin at 1250 rpm in IEC model CRU-5,000 swinging-bucket (rotor #253) centrifuge at room temperature for 40 minutes (or equivalent G force). Aspirate cell layer between saline and Ficoll-Hypaque. Wash cells with PFS using 1400 rpm (or equivalent G force) to spin cells down, decant, resuspend in PFS, spin at 1000 rpm (or equivalent G-force), pool all tubes, and repeat last step.

(c) After third centrifugation, resuspend in 50 ml of Minimal Essential Medium (MEM). Count cells using Coulter Counter (or equivalent method using hemocytometer).

(d) Prepare sample for cytocentrifuge in 1% human serum albumin. Adjust concentration of cell preparation to $5 \times 10^6$/ml. Stain cytocentrifuge preparation with Wright's stain and make the differential cell count under oil on 300 cells. If the preparation contains 15% or less monocytes or more than 10% granulocytes, discard it and select another donor.

4. Control Incubations (a) Pipette 5 ml of cell suspension into each 25 cm$^2$ sterile polystyrene plastic flask (Corning or Falcon). The flasks must have been "aged" for 6 months because new flasks may contain inhibitory plasticizers and residual oxidants. Immediately place the flasks with the flat surface down. Ensure continued mixing as cells are added to the flasks.

(b) Cell control. This flask contains cells without additions: add a volume of MEM to match the volume of test materials. Usually this would be 0.5 ml (10% of the total volume) or less. (see 5a).

(c) Serum control. This flask contains cells +5% heat-inactivated AB serum (0.25 ml).

(d) Staphylococcal control. This flask contains 100 microliters of a standardized staphylococcal cell preparation +5% fresh AB serum.

5. Incubations with Unknowns (suspected pyrogens or materials being tested)

(a) Cells+unknown. The material to be tested is added to a flask at a concentration which corresponds to the quantity per kilogram of body weight per $10^6$ mononuclear cells. For example, if a pharmaceutical is to be given parenterally at 5 mg/kg, the concentration added to the flask would be 5 mg/$10^6$ mononuclear cells or 125 mg/$25 \times 10^6$ cells.

(b) Cells+unknown in 5% heat-inactivated AB serum. Same as 5a, but cells have additional AB serum (5% v/v or 0.25 ml per flask).

6. Incubation procedures. Flasks are incubated at 37° C.±0.5° C., 5%±1% $CO_2$-95% humidified air on a flat surface with screw caps ½ turn less than tight. Incubation is for 48±2 hours.

7. Processing of supernates. Supernates are poured into sterile conical 15 ml polystyrene centrifuge tubes and centrifuged at 2500×g for 30 minutes. The supernatant is rapidly poured into another tube and sodium azide added [0.02% (w/v) final concentration] and kept at 2° to 6° C. Supernates are to be assayed within 6 weeks. Assays of LP do not require freezing at −70° C. For shipment, all samples should be frozen at −70° C. and packed in Dry-Ice.

8. Assay of LP in Supernatant Medium by Rabbit Injections of Unfractionated Materials (a) Rabbits. Rabbits are approximately 3 kg (±500 grams), albino, New Zealand-derived, virgin females. Rabbits are housed in individual cages at 69° F.±1° F. and trained in metal restrainers for 3 days prior to use. Details concerning food, water, and care are given in the notes at the end of this section.

(b) Training. Following arrival of a rabbit shipment, rabbits are rested 48 hours to allow for environmental adjustment prior to training. Training consists of 3 consecutive days. Day 1, restainer for 4 hours. Day 2, restrainer for 6 hours. Day 3, restrainer with rectal probe for 4 hours. Also on day 3, 5.0 ml of PFS is injected by intraveneous bolus and temperature is recorded. Before any injection, rabbits must not vary more than 0.3° C. during the 36 minutes prior to injection.

This is the minimum training program. Once LP or supernate injections begin, rabbits are not to be rested more than 24 hours as longer periods may require retraining.

(c) Selection of Rabbits. On day 4, rabbits are given a standardized injection (i.v.) of semipurified, standardized human LP stabilized in 0.1% heat-inactivated rabbit serum (see notes). Rectal temperatures are recorded. This is repeated on days 5 and 6. Since the standardized LP preparation is stable for several months, comparisons can be made for the selection of low responders, high responders, or rabbits with unstable base-line temperatures following injections. Rabbits which on three standardization tests fail to demonstrate mean peak fever of less than 0.5° C. within 60 minutes following i.v. bolus injection are rejected. Likewise, rabbits which on three standardization tests exceed a mean of 1.0° C. peak fever over baseline are also rejected.

(d) Determination of base-line temperature. The base-line temperature is determined by the temperature immediately before and after the injection. Temperatures are recorded every 8 minutes. If the temperatures are not the same, then the two readings preceding the injection are used. If these are not the same, then the mean of the two preceding and reading following the injection is calculated.

(e) Rabbit injection schedule. Rabbits are placed in restrainers between 10 and 11 a.m. Injections are given after 1 hour (but not later than 2 hours) after insertion of rectal probes. The following schedule is to be followed: Day 4, 5 and 6=LP control injections. Day 7=cell control. Day 8=cells+hGH. Day 9=cells+AB serum. Day 9 (providing baselines are <0.3° C. from injection time to T=56 minutes)=STAPH control. Day 10=cells+AB serum+hGH. Days 11-13, additional samples containing serum as indicated. No rabbits are used in LP assays for supernates containing serum after day 13. Rabbits are discarded on day 14.

(d) Determination of peak fever. Peak fever is the highest recording above base-line within 56 minutes following injection. Peak readings occurring at 64 minutes or later invalidate the test, as this is not typical LP fever. (Recording equipment and calibrations are discussed in the notes that follow.)

(g) Significance of peak fever. Peak fever is a biologic quantitation of the amount of LP in the supernate. Three rabbits are used to assay a sample, and the mean is calculated. Means fever of less than 0.3° C. is not considered significant. A mean peak above 0.3° C. is considered evidence that the cells were stimulated to produce LP in vitro.

(h) Injections of control incubations. (From 4a, 4c, and 4d). Calculations are made from the percentage of monocytes determined in the donor cell preparation. Each rabbit is injected with the supernate derive from $3 \times 10^6$ monocytes (or $1 \times 10^6$/kg). Cell control (4b) is injected into three rabbits. (4b) and (4c) should not yield mean fevers of 0.3° C. or greater. Otherwise, the entire assay must be rejected, since this indicates that auto-stimulation has occurred. Staphylococcal control (4d) is likewise injected into three rabbits. Peak fevers should have a mean of 0.5°-0.9° C. A mean peak of less than 0.5° C. indicates poor cell response to a standard stimulus and invalidates this assay.

(i) Injections of incubations with unknowns. 5a can be injected into rabbits at $3 \times 10^6$ monocytes per 3 kg rabbit. Mean peak fever of 0.3° C. or greater indicates a positive response and implicates the presence of a contaminating pyrogenic agent or that the pharmaceutical itself is capable of inducing LP. (5b) is similarly injected and results are calculated as in (5a).

9. Interpretation of Results with Statistical Considerations

Mean peak fever. Once the base-line has been established, the highest reading is recorded as peak. Although rises of 0.1° or 0.2° C. are not considered significant, these numbers are entered when calculating the mean peak fever (see 8e). The mean and standard deviation are calculated as follows:

$$\bar{X} = \frac{\Sigma X_i}{N}$$

$$S.D. = \sqrt{\frac{\Sigma(X_i - \bar{X})^2}{N-1}}$$

The standard error of the mean (SEM) is $SD/\sqrt{N}$.

NOTES (to preferred embodiment presented above)

1. Sterile Technique. Standard methods for sterile, aseptic methods in the laboratory are to be followed. Cell incubation procedures in dispensing cells and additives into incubation flasks are carried out in a laminar flow hood or equivalent suitable hood for tissue culture methods.

2. Glassware, reagents, disposable plastics, and related materials. All glassware is washed, rinsed in pyrogen-free water, covered with aluminum foil, and baked at 180° C. for 4 hours to inactivate endotoxins. All plastics are purchased as sterile and pyrogen-free. All neeles and syringes are purchased as sterile and pyrogen-free. Processing of fluids not purchased as pyrogen-free is accomplished by autoclaving for 45 minutes and testing for endotoxins using the Limulus amebocyte lysate test (LAL) (see note 3). Sephadex G-50 (fine) is autoclaved for 1 hour in PFS and rinsed in 4 volumes PFS. Sterilization of glass columns used for gel-filtration is carried-out using a 24-hour exposure to 10% (w/v) formaldehyde followed by a 4-volume rinse with PFS. All tubing for gel-filtration is purchased as sterile and pyrogen-free. (Abbott Venipac, Chicago, IL).

3. LAL. The LAL lysate is purchased from Associates of Cape Cod (Woods Hole, MA) as lyophilized powder and reconstituted in PFW (pyrogen-free water). Aliquots (0.1 ml fractions) are stored in $75 \times 10$ mm baked glass tubes covered with a small square of aluminum foil. Reconstituted lysate is kept at −70° C. and thawed only once. A preparation of *E. coli* endotoxin (RE-2, Bureau of Biologics) is used as a standard. All LAL testing is carried out using 0.1 ml of dilutions of materials in PFW, and incubations are for 1 hour at $37 \pm 0.5°$ C. in a stationary water bath. Tubes are read immediately by inversion (180°) to determine the presence of a firm "clot.⇌

4. Media. The culture medium is minimal essential medium (MEM); Earl's balanced salts with 2 mM L-glutamine containing phenol red, 100 units Penicillin G/ml, and 100 μg Streptomycin/ml with 0.01 M HEPES buffer. These regeants may be purchased from Microbiological Associates (Walkersville, MD). Lot numbers are recorded and each Lot of MEM (contining Penicillin, Streptomycin, and HEPES buffer) is tested by the LAL test prior to being used in cell incubations. Lots containing 50 pg or greater endotoxin/ml using the LAL test are not used. For these studies, LOT 1 K029 has been tested and found acceptable (Expiration date May 30, 1984).

5. Ficoll-Hypaque. Ficoll (Pharmacia Fine Chemicals, Piscataway, NJ) as a 9% (w/v) solution in water is autoclaved for 30 minutes and stored at room temperature. Hypaque (Winthrop Laboratories) is warmed to 37° C., and a 33.9% (w/v) solution is stored at room temperature. Ficoll-Hypaque is made by combining 24 ml of Ficoll with 10 ml of Hypaque prior to use.

6. Human Serum Albumin (HSA). HSA is obtained as a 25% (w/v) solution from Abbott Laboratories, and a 1% w/v solution is made by dilution in PFS. Lot numbers are recorded.

7. Wright's Stain. Wright's stain is obtained as a premixed solution from Fisher Chemicals. Cells are airdried for 30 minutes following cytocentrifugation and stained with Wright's stain. Slides are flooded with 1 ml of stain for 2 minutes on a level platform; then 1 ml of PFW is added, allowed to mix thoroughly, and remain for 4 minutes. Slides re rinsed, dried, and then examined under an oil immersion lens.

8. Microscopic differential counts. Microscopic differential counts are made using a 300-cell count. Cell differentials are based on typical cell morphology by a trained laboratory technician with demonstrated expertise in hematological examination confirmed by a laboratory supervisory certified by the American Association of Hematological Assistants.

9. Cytocentrifuge (Cytospin). The cytocentrifuge used in these studies was obtained from Shandon Scientific Products, Sewickley, PA, and was operated at speeds suggested by the manufacturer as optimal for human blood specimens. For assays a speed of 400 RPM for 5 minutes may be used.

10. Coulter counter. A Coulter-Counter (TM) from Coulter Electronics, Hialeah, FL, was used in these studies. The settings for assays should be a cell aperture determined optimal for counting human blood leukocytes. The counter should be standardized every two weeks using a known standing suspension of particles through a certified service contract with Coulter Electronics.

11. Centrifuges. Centrifuges used in these studies were IEC model CRU 5000 for cell separations and a Beckman J-21 for higher speeds.

12. Heat-inactivated human AB serum pool. AB blood donors are bled in the morning (fasting), and the blood is allowed to clot at room temperature for two hours in 50 ml glass tubes. The clot is then allowed to retract in the cold (2°–8° C.) for two hours. Tubes are then spun at $1,000 \times g$ at 2°–8° C. for 30 minutes, and the serum is removed by pipetting in a hood into a serile beaker. Care is taken not to contaminate the serum preparation with red cells. The pooled serum is aliquoted into 10 ml sterile pyrogen-free polypropylene tubes ($170 \times 25$ mm). Tubes are immersed in $56 \pm 1.0°$ C. water bath for 30 minutes. These are then aliquoted and frozen at $-20 \pm 4.0°$ C. and used as heat-inactivated AB serum. Each aliquot is thawed once and not refrozen.

13. Fresh AB serum. Fresh AB serum consists of the same pool of AB serum aliquoted in 5.0 ml volumes in $170 \times 25$ mm polypropylene tubes and frozen at $-70° \pm 10°$ C. Each aliquot is thawed once and not refrozen.

14. Heat-killed Staphylococcus albus.

(1) Purpose. This section describes the methods involved in the preparation of killed *Staphylococcus albus* for use in stimulating human mononuclear cells for the in vitro production of leukocytic pyrogen.

(2) Equipment Required. Shaking water bath at 37° C. 50 ml conical centrifuge tubes, plastic, pyrogen-free; centrifuge (3000 RPM in 25 radium heat); flasks (4 liter); pipettes; vortex apparatus; tubes; spectrophotometer.

(3) Reagents Required. Trypticase soy broth (TSB) (Microbiological Associates, Rockville, MD); 0.9 NaCl%, sterile, pyrogen-free (Baxter-Travenol, Morton Grove, IL); *Staphylococcus albus* culture (skin isolate from Tutfs-New England Medical Center Hospital, Department of Bacteriology). This isolate is confirmed as *Staph. albus* by negative coagulase test, negative protein A. Certified by Department of Bacteriology, Tufts University. Alternate source of *Staphylococcus albus* is American Type Culture Collection, Rockville, MD.

(4) Procedure (a) A single colony on blood agar is subcultured in 10 ml of TSB, incubated at $37°$ C.$\times 4$ hours, and then added to 2,000 ml TSB in a 4,000 ml flask with sterile cotton plugging. The TSB is autoclaved prior to use for 45 minutes.

(b) The inoculated TSB is shaken gently for 48 hours in a 37° C. water bath.

(c) The milky suspension is spun in 250 ml plastic tubes at $2,500 \times G$ for 30 minutes. The supernate is discarded, and the bacterial pellet resuspended in 0.9% NaCl to the original volume. A repeat centrifugation is carried out, and the supernatant discarded.

(d) The bacterial pellets are resuspended in 0.9% NaCl to a total volume of 500 ml and boiled for 1 hour. After cooling to room temperature, the suspension is spun at $2,500 \times G$ for 30 minutes, and the supernate discarded. This procedure of resuspension and centrifugation is repeated twice. The final pellets are resuspended in 0.9% NaCl to a volume of 100 ml and the O.D. assessed in a Beckman spectrophotometer at 530 nm. Volumes of 0.9% NaCl are added until the O.D.$=3.30$. A saline blank is used.

(e) After adjustment of the O.D., the suspension is aliquoted into 10 ml tubes and frozen at $-20°$ C.

(5) Quality Control.

(a) Following adjustment with 0.9% NaCl to an O.D. of 3,30, a sample (0.1 ml) is plated onto blood agar (Gibco, Grand Island, NY) and checked for sterility.

(b) A sample of the killed staphylococcal cell suspension is also added to human mononuclear cells ($5 \times 10^6$/ml) at a final concentration of 2% and smears made on glass slides. These smears are stained with Wright's stain.

(c) Smears are examined at $970 \times$ and the bacteria:leukocyte ratio is assessed.

(d) The bacteria:leukocyte ratio must be in the range 10:1 to 20:1.

(e) The frequency of quality control is one per batch of suspension made. All batches are labeled with the date.

(f) Suspensions frozen at $-20°$ C. are thawed prior to use, and suspensions are usable for 1 year.

15. LP Standard. For an assay a preparation of LP is made and purified as follows. Two plateletpheresis byproducts are obtained from the American Red Cross. Ficoll-Hypaque separation is performed after the WBC concentration is adjusted in PFS to $5,000 \pm 500$/mm$^3$. The mononuclear layer is aspirated, washed and resuspended in MEM at $20 \times 10^6$ cells/ml. Fresh AB serum is added (5% v/v) along with heat-killed *Staphylococcus albus* (5% v/v) in a 1000 ml flask, which is then shaken gently at $37 \pm 1.0°$ C. for 1 hour. Cells are spun in 50 ml polypropylene tubes at 1,000 RPM (IEC-CRU-5000 or equivalent G force) for 5 minutes. The supernate is discarded. The cells are resuspended at $3 \times 10^6$ cells/ml in fresh MEM and pipetted onto the flat glass surface of pharmacy bottles or plastic petri dishes at $5 \times 10^5$ cells/cm$^2$. After one hour at $37 \pm 1.0°$ C., $5\% \pm 1.0\%$ CO$_2$ in a stationary incubator, the non-adherent cells are poured off by gentle physical rotation, and the adherent cells are covered with a replacement volume (same as removed) of MEM. The adherent cells are now allowed to incubate at 37±1° C. for the next 24±2 hours in 5±1.0% $CO_2$, humidified air. Cell supernates are spun at 10,000×G. for 30 minutes at 4° C. Sodium azide (0.02%, w/v) is added to cell-free supernate and stored at 4°-8° C. for 1-2 days. Cell supernate (1,000 ml) is concentrated in standard autoclaved dialysis tube (30 min, Union Carbide, Chicago, IL) in front of two high speed fans in a hood until the volume is reduced to 50 ml. Gel-filtration using a 170×5.0 cm glass column packed with autoclaved Sephadex G-50 (fine) is accomplished during two chromatographic separations of 25 ml each of the concentrated cell supernate. Cytochrome C (horse type VI, Sigma, St. Louis, MO) is added at 1% (w/v) to a concentrated LP sample from a stock of 10% (w/v) filtered, sterile solution. The column is equilibrated and run in 0.1% (w/v) polyethylene glycol [MW 4,000 to 6,000 (Kodak, Rochester, NY) from a stock of 10% (w/v) which had been autoclaved for 1 hour], 0.9% unbuffered PFS, 4° C. Fractions are collected in sterile, pyrogen-free glass tubes containing enough heat-inactivated normal rabbit serum (see below) to have a final concentration in each fraction at 1% (v/v). The 12,000-15,000 dalton peak [as previously reported-Dinarello et al., J. Exp. Med., 129:1369 (1974)] is pooled and stored at 2°-8° C. in 0.02% (w/v) sodium azide. The two chromatographic runs are pooled.

The amount of LP necessary to produce a peak fever in 9 rabbits between 0.6° and 0.9° C. on three consecutive days is determined. This amount is now considered the LP standard for a 4 month±2 week period since pervious studies have established the stability of these preparations.

The normal rabbit serum used to stabilize the LP is obtained from cardiac puncture bleeding of fresh rabbits. Blood is allowed to clot in sterile, glass, 50 ml tubes as described for human AB serum. Rabbit serum is inactivated at 56±1° C. for two hours. It is stored at −20±4° C.

16. Yellow Springs Instrument Telethermometer Calibration. YSI Scanning Eleven Channel Telethermometer model #47 is calibrated using a calibrated thermometer in a water bath at temperatures between 35° and 40° C. Calibrations are made weekly. A YSI model 80 recorder is attached and is calibrated every day prior to rabbit testing.

17. Probe Selection. The thermocouple end (5±1 cm) of YSI probes Model 401 are placed in a water bath adjacent (1±0.5 cm) to a calibrated thermometer and the jack inserted into the telethermometer. Water bath temperatures are varied from 38° to 41° C. and readings observed for 1 minute. Probes not properly reading are rejected. (Probes are retested every 4 weeks).

18. Rabbit Housing, etc. Rabbits are given a physical examination by a registered veterinary nurse upon arrival. Rabbit stools are cultured for pathogens. Rabbits suspected of illness or infection are rejected. Once selected, rabbits are housed in individual cages with standard rabbit food and water ad libitum. Dried farm grass (hay) is supplemented ad libitum to help form fecal pellets. Room temperature is maintained (and recorded) at 69±1° F. Day cycle is from 6 a.m. to 6 p.m. and night cycle from 6:01 p.m. to 5:59 a.m. Pyrogen testing is carried out in the same room as housing. During pyrogen testing, only authorized personnel are allowed to enter the room.

Having now generally described this invention, the same will be better understood by reference to certain specific examples, which are included herein for purposes of illustration only and are not intended to be limiting of the invention or any embodiment thereof, unless specified.

Example: Determination of the Pyrogenicity of Methionyl-Human Growth Hormone Preparation by the In Vitro Productin of Leukocytic Pyrogen From Human Mononuclear Cells Human growth hormone, biosynthetically produced by a recombinant strain of *E. coli* as a N-terminal methionyl analog, has recently been used in Phase I clinical trails. The preparation used, Genentech Lot 002A1, produced considerable pain approximately 2 hours following intramuscular injection, with subsequent chills and fever. In addition, in these subjects the total number of neutrophils and monocytes was increased and serum iron, albumin, and hematocrit were decreased. These findings suggest that human Growth Hormone (hGH) Lot 002A1 induced an acute inflammatory response at the injection site with characteristic sequelae; namely, fever, leukocytosis, and hypoferremia. Of importance is the fact that hGH Lot 002A1 was negative in the USP standard rabbit pyrogen test. Furthermore, the Limulus amebocyte lystate test for the presence of endotoxin revealed less than 500 pg endotoxin/mg of methionyl-hGH Lot 002A1. Considering that each subject received 8 mg of Lot 002A1, the maximum amount of endotoxin in each injection was 4 ng. In control experiments using human volunteers, 200 to 300 ng (3 to 4 ng/kg) of *E. coli* endotoxin administered intravenously produces fever, chills, leukocytosis, and hypoferremia; and typhoid vaccine, which contains microgram quantities of endotoxin, produces similar reactions when administered subcutaneously to humans. Thus, it is unlikely that endotoxin contamination accounted for the acute inflammatory response observed in the subjects. It is probable, however, that Lot 002A1 was contaminated with another *E. coli* product other than endotoxin, and, since the acute toxicity studies and rabbit pyrogen test were negative, such a substance is apparently more pyrogenic for humans than for laboratory animals. Accordingly, the method of the invention using in vitro production of leukocytic pyrogen from human mononuclear cells was tested by its ability to predict the pyrogenicity of hGH Lot 002A1 when its pyrogenicity was not predicted from the currently available standard tests.

MATERIALS AND METHODS

Human Mononuclear Leukocytes

Human subjects taking no medication were bled via antecubital vein into 60 ml heparinized syringes (10 units heparin/ml final concentration). The blood was diluted with 2 parts 0.9% NaCl and layered over Ficoll-Hypaque in 50 ml conical plastic tubes. After centrifugation, the interphase containing the mononuclear cells was aspirated, washed twice in 0.9% NaCl, and resuspended at a concentration of 5×10$^6$ cells/ml in Minimal Essential Medium Eagle (Microbiological Associates, Walkersville, MD) containing 0.1 M HEPES buffer, 100 units/ml penicillin and 100 μg/ml streptomycin. Differential cell counts were done using a cytocentrifuge. Preparations consistently contained 20 to 25% monocytes, 70 to 75% lymphocytes, and 5 to 10% neutrophils. 5 ml of cells was aliquoted into each 25 cm² culture flask (Millipore, Bedford, MA). The following procedure was used for each experiment: (a) cell control flask, (b) staphlococcal control flask, and (c) hGH containing flasks. The staphlococcal flask served as a positive control to ascertain the viability of the cell preparations and their ability to produce LP under stimulation by staphylococci. *Staphylococcus albus* was prepared as described by Root et al., *J. Lab. Clin. Med.*, 150:709–714 (1970), which is herein incorporated by reference. The *S. albus* suspension was killed by boiling for 1 hour and during several subsequent washes. A single stock preparation of killed staphylococci was used in all experiments, and the amount added to each flask was sufficient for a bacteria:-leukocyte ratio of 20:1. In addition, flasks with cells and staphylococci also contained 5% AB serum for opsonization. A single source of fresh AB serum was used in these studies and kept frozen at $-70°$ C. until thawed for use.

Incubations were for 24 to 48 hours at 37° C., 5% $CO_2$. Thereafter, cell cultures were centrifuged at $2,200 \times G$ for 30 minutes. The supernatant medium removed, stored at 4° C., and assayed in rabbits within 48 hours.

Pyrogen Assays

All glassware, plastic materials, and media were sterile and pyrogen-free. Housing of rabbits and conditions of temperature recordings have been described previously in Wolff et al, *J. Lab. Clin. Med.*, 65, 268–276 (1965), which is herein incorporated by reference. Briefly, rabbits were New Zealand albino females weighing 2.5 to 3.0 kg. They were trained in metal restrainers for 3 days prior to testing. Rectal thermistors were inserted 8 to 10 cm and held in place by elastic bands. Rectal temperatures were recorded every 12 minutes. All injections were via marginal ear vein as a bolus. Three rabbits were used to test each supernate. Data were derived from the peak rise in rectal temperature over base-line rectal temperature. Base-line rectal temperatures were recorded 1.5 to 2 hours prior to injection. Rabbit responses of fever peak levels occurring more than 60 minutes after injection were discarded, since human LP produces peak fever 48 to 60 minutes following injection. The straight-line dose-response relationship for human LP producing fever in rabbits has been established, and peak fevers above baseline temperature of 0.4 to 0.8° C. can be used for quantifying amounts of LP in supernates.

Limulus Amebocyte Lysate (LAL) Test

A single preparation of LAL was used throughout these studies. It was obtained from Associates of Cape Cod, Woods Hole, MA, as Lot 52-80-248 with a sensitivity of 0.025 ng/ml. The procedure used for the LAL test was as described in Elin and Wolff, *J. Inf. Dis.*, 128:349–352 (1973), which is herein incorporated by reference. Preparations of hGH were dissolved in pyrogen-free water at a concentration of 5 mg/ml, and 10-fold dilutions in pyrogen-free water were carried out. To 100 μl of LAL, 100 μl of the hGH dilution was added, incubated at 37° C. for 1 hour, and read immediately. Endotoxin controls were used at 5, 0.5, 0.05, and 0.025 ng/ml. The endotoxin used in these studies was obtained from the Bureau of Biologics as RE-2 (*E. coli* National Reference endotoxin). Inhibition controls were included in all LAL tests on hGH at 0.5 ng/ml endotoxin in the presence of undiluted hGH.

hGH Preparations

These were received from Genentech as a lyophilized powder and reconstituted with MEM or pyrogen-free water to 5 ng/ml. Since the mononuclear cell incubations were in flasks containing 5 ml, 0.5 ml of sample was added to flasks. In order to maintain a constant volume, 0.5 ml MEM was added to cell control flasks.

Results

The Effect of hGH on LP Production From Human Mononuclear Cells in Vitro

The initial experiments are shown in Table I. In these two studies, concentrations of hGH Lot 002A1 were 0.01 and 0.1 mg/ml. After 24 hours of incubation, there was no evidence of LP production. However, the staphylococcal control incubations produced LP at expected levels. Two factors could account for the results shown in Table I: (1) at the concentration of 0.1 mg/ml hGH, the amount of contaminant was not sufficient to stimulate LP production and/or (2) the time of in vitro exposure was not sufficient to stimulate lymphokine production. In this latter situation, if the time were extended, the production of LP from monocytes would be expected to occur via stimulation from lymphocyte products as has been shown by Dinarello et al., *J. Exp. Med.*, 153:1215–1224 (1981), which is herein incorporated by reference. This publication indicates that extension of incubation time beyond 24 hours, using incubation methods known prior to the present invention, would be expected to lead to false positives due to autostimulation, and that such an extension of time could not be carried out without adversely affecting the reliability of the test.

TABLE I

| Effect on hGH (002A1) on LP Production from Human Mononuclear Cells in vitro. | |
|---|---|
| Incubation[a] | $\Delta T(°C.)$[b] |
| Cells[c] | 0.0 (3) |
| Cells and staphylococci[d] | 0.55 ± 0.08 (6) |
| Cells and hGH (0.1 mg/ml)[d] | 0.05 ± 0.05 (6) |
| Cells and hGH (0.01 mg/ml)[d] | 0.0 (6) |

[a]24 h at 37° C.
[b]Mean (±SEM) peak rise in rabbit rectal temperature produced by each supernate; number in parentheses indicates number of rabbits used to assay each supernate. Each rabbit received the equivalent supernate from 6 × 10⁶ mononuclear cells.
[c]5 × 10⁶ human mononuclear cells/ml.
[d]mean of two separate experiments.

The concentration of endotoxin in these preparations of hGH 002A1 was determined just prior to addition to mononuclear cell cultures. In three separate LAL tests, gelation occurred in concentrations equivalent to 200 pg endotoxin/mg hGH using the RE-2 Reference preparation.

Effect of Pituitary-Derived hGH on LP Production From Human Mononuclear Cells in Vitro Pituitary hGh was tested in order to ascertain whether the stimulation of LP production by hGh 002A1 was due to high concentrations of growth hormone and not due to the effect of a possible contaminant. hGH obtained from Kabi Pharmaceuticals was used at a concentration of 0.3 mg/ml in human mononuclear cell cultures under the same conditions which stimulated LP production from Lot 002A1 shown in Table II.

TABLE II

Dose-Response Relationship of hGH (002A1) on
Production of LP from Human Mononuclear Cells in vitro.

| Incubation[a] | ΔT(°C.)[b] |
|---|---|
| Cells[c] | 0.0 (9) |
| Cells and staphylococci | 0.57 ± 0.08 (3) |
| Cells and hGH (0.1 mg/ml) | 0.0 (3) |
| Cells and hGH (0.2 mg/ml) | 0.50 ± 0.10 (3) |
| Cells and hGH (0.5 mg/ml) | 0.96 ± 0.03 (3) |
| Cells and excipient medium | 0.0 (3) |

[a] 48 h at 37° C.
[b] Mean (±SEM) peak rise in rabbit rectal temperature produced by each supernate; number in parentheses indicates number of rabbits used to assay each supernate. Each rabbit received the equivalent supernate from 6 × 10⁶ mononuclear cells.
[c] 5 × 10⁶ human mononuclear cells/ml.

As depicted in Table III, pituitary-derived hGH (Kabi) did not stimulate LP production. The ability of these cells to produce LP using the staphylococcal stimulus is also known. These results indicate that high concentrations of growth hormone do not stimulate LP production. The implication of this experiment is that the effect of hGH 002A1 on LP production is likely due to either a bacterial contaminant or the unique N-terminal methionyl configuration of biosynthetic hGH.

TABLE III

Effect of Pituitary Derived hGH on LP
Production from Human Mononuclear Cells in vitro.

| Incubation[a] | ΔT(°C.)[b] |
|---|---|
| Cells[c] | 0.0 (3) |
| Cells and staphylococci | 0.53 ± 0.06 (3) |
| Cells and hGH (0.3 mg/ml)[d] | 0.0 (3) |

[a] 48 h at 37° C.
[b] Mean (±SEM) peak rise in rabbit rectal temperature produced by each supernate; number in parentheses indicates number of rabbits used to assay each supernate. Each rabbit received the equivalent supernate from 6 × 10⁶ mononuclear cells.
[c] 5 × 10⁶/ml.
[d] Obtained from Kabi Pharmaceuticals.

Effect of Different Preparations of hGH on LP Production from Human Mononuclear Cells in Vitro Two additional preparations of biosynthetic hGH were purified and tested for their ability to stimulate human LP in vitro. As shown in Table IV, Lots GO111-28 and 004 at concentrations of 0.5 mg/ml induced LP production.

TABLE IV

Effect of Different Preparations of hGH on LP
Production from Human Mononuclear Cells in vitro.

| Incubation[a] | ΔT(°C.)[b] |
|---|---|
| Cells[c] | 0.0 (3) |
| Cells and staphylococci | 0.53 ± 0.04 (3) |
| Cells and hGH (GO111-28, 0.5 mg/ml) | 0.56 ± 0.03 (6) |
| Cells and hGH (004, 0.5 mg/ml) | 0.43 ± 0.03 (3) |

[a] 48 h at 37° C.
[b] Mean (±SEM) peak rise in rabbit rectal temperature produced by each supernate; number in parentheses indicates number of rabbits used to assay each supernate. Each rabbit received the equivalent supernate from 6 × 10⁶ mononuclear cells.
[c] 5 × 10⁶/ml.

Effect of Isoelectric Focusing of hGH on Ability to Induce LP Production from Human Mononuclear Cells in Vitro.

A preparation of N-methionyl hGHG was focused, eluted, and lyophilized. Using the same concentration of hGH and conditions which stimulated LP production by Lots 002A1, GO111-28, and 004, 0.5 mg/ml focused hGH did not induce human LP in vitro. These results are shown in Table V. Negative cell controls and positive staphylococcal controls indicated that these cells were capable of releasing LP when stimulated by phagocytosis. These data provide evidence that (1) N-terminal methionyl hGH is not itself capable of inducing human LP and (2) the agent(s) which is responsible for stimulating LP production is separable by isoelectric focusing or other methods.

TABLE V

Effect of Isoelectric Focusing of hGH on
Ability to Induce LP Production from Human
Mononuclear Cells in vitro.

| Incubation[a] | ΔT(°C.)[b] |
|---|---|
| Cells[c] | 0.0 (3) |
| Cells and staphylococci | 0.53 ± 0.06 (3) |
| Cells and hGH (0.5 mg/ml) | 0.0 (3) |

[a] 48 h at 37° C.
[b] Mean (±SEM) peak rise in rabbit rectal temperature produced by each supernate; number in parentheses indicates number of rabbits used to assay each supernate. Each rabbit received the equivalent supernate from 6 × 10⁶ mononuclear cells.
[c] 5 × 10⁶/ml.

Ability of Heat-Inactivated Human Serum to Enhance the Production of LP in Vitro Induced by Preparations of hGH.

In the previous studies all preparations of biosynthetic hGH were incubated in the absence of human serum. Activation of LP synthesis by many exogenous pyrogens in vitro takes place in serum-free media, while other activators require the presence of 5 to 15% isologous serum. In models of tuberculin or penicillin sensitivity, LP production in vitro is dependent on the presence of specific antibodies. In other experiments, the presence of human serum prevents the release of LP by certain stimulators. Therefore, experiments were carried out to ascertain the requirement of human serum for preparation of hGH to stimulate LP production. As shown in Table VI, Lots 0111-26, 002A2, and 003A1 induced LP synthesis only in the presence of 5% heat-inactivated (56° C., 30 min.) human AB serum.

TABLE VI

Ability of Heat-Inactivated Human Serum to
Enhance the Production of LP in vitro Induced by
Preparations of hGH.

| Incubation[a] | ΔT(°C.)[b] |
|---|---|
| Cells[c] | 0.0 (3) |
| Cells and staphylococci | 0.70 ± 0.10 (3) |
| Cells and hGH (0111-26; 0.1 mg/ml) | 0.0 (3) |
| Cells and hGH (0111-26 0.1 mg/ml, 5% ΔAB serum) | 0.60 ± 0.15 (3) |
| Cells and hGH (002A2 0.5 mg/ml) | 0.0 (3) |
| Cells and hGH (002A2, 0.5 mg/ml, 5% ΔAB serum) | 0.63 ± 0.03 (3) |
| Cells and hGH (003A1 0.5 mg/ml) | 0.0 (2) |
| Cells and hGH (003A1, 0.5 mg/ml, 5% ΔAB serum) | 0.56 ± 0.03 (3) |

[a] 48 h at 37° C.
[b] Mean (±SEM) peak rise in rabbit rectal temperatures produced by each supernate; the number in parentheses indicates the number of rabbits used to assay each supernate. Each rabbit received the equivalent supernate from 6 × 10⁶ mononuclear cells.
[c] 5 × 10⁶/ml.

Effect of Different Preparations of hGH on LP Production from Human Mononuclear Cells in Vitro.

In Table VII, results are depicted after screening nine different lots of biosynthetic hGH purified by various methods on their ability to induce LP production in vitro. Because previous studies had indicated that the presence of 5% heat-inactivated AB serum enhanced the ability of certain preparations of hGH to induce LP production, the incubations were carried out with or without serum. Concentrations of hGH and time of incubations were performed as demonstrated previously. In Table VII, three parparations of hGH are shown which did not stimulate LP production. These are Lots K0386, 316-2-1 and 316-2-2, and their inability to stimulate LP production is not dependent on the absence of serum. A possible interpretation of these results is that the purification procedures used for these lots have removed or destroyed the pyrogen-inducing material(s) present.

TABLE VII

Effect of Different Preparations of hGH on LP Production from Human Mononuclear Cells in vitro.

| Incubation[a] | $\Delta T(°C.)$[b] |
|---|---|
| Cells[c] | 0.05 (5) |
| Cells and staphylococci | 0.73 ± 0.06 (3) |
| Cells and hGH (CS-363, 0.5 mg/ml) | 0.70 ± 0.0 (3) |
| Cells and hGH (CS-363, 0.5 mg/ml, 5% $\Delta$AB Serum) | 0.63 ± 0.03 (3) |
| Cells and hGH (RP 390, 0.5 mg/ml) | 0.40 ± 0.0 (3) |
| Cells and hGH (RP 390, 0.5 mg/ml, 5% $\Delta$AB Serum) | 0.36 ± 0.06 (3) |
| Cells and hGH (KO 386, 0.5 mg/ml) | 0.0 (3) |
| Cells and hGH (KO 386, 0.5 mg/ml, 5% $\Delta$AB Serum) | 0.0 (3) |
| Cells and hGH (316-2-1, 0.5 mg/ml) | 0.0 (3) |
| Cells and hGH (316-2-1, 0.5 mg/ml, 5% $\Delta$AB Serum) | 0.0 (3) |
| Cells and hGH (316-2-2, 0.5 mg/ml) | 0.0 (3) |
| Cells and hGH (316-2-2, 0.5 mg/ml, 5% $\Delta$AB Serum) | 0.0 (3) |
| Cells and hGH (316-2-3, 0.5 mg/ml) | 0.0 (2) |
| Cells and hGH (316-2-3a, 0.5 mg/ml) | 0.20 ± 0.0 (3) |
| Cells and hGH (316-2-3a, 0.5 mg/ml, 5% $\Delta$AB Serum) | 0.53 ± 0.03 (3) |
| Cells and hGH (316-2-4, 0.5 mg/ml) | 0.36 ± 0.03 (3) |
| Cells and hGH (316-2-4, mg/ml, 5% $\Delta$AB Serum) | 0.60 ± 0.0 (2) |
| Cells and hGH (316-2-4a, 0.5 mg/ml) | 0.70 ± 0.05 (3) |
| Cells and hGH (316-2-4a, 0.5 mg/ml, 5% $\Delta$AB Serum) | 0.40 ± 0.13 (3) |
| Cells and hGH (316-2-5, 0.5 mg/ml)[d] | 0.15 ± 0.07 (6) |
| Cells and hGH (316-2-5, 0.5 mg/ml, 5% $\Delta$AB Serum)[d] | 0.28 ± 0.11 (6) |

[a] 48 h at 37° C.
[b] Mean (±SEM) peak rise in rabbit rectal temperature produced by each supernate; number in parentheses indicates the number of rabbits used to assay each supernate. Each rabbit received the equivalent supernate from $6 \times 10^6$ mononuclear cells.
[c] $5 \times 10^6$/ml.
[d] Mean of two separate experiments.

DISCUSSION

These results indicate (1) that certain lots of methionyl-hGH are capable of inducing LP production from human mononuclear cells in vitro and (2) after specialized purification procedures, other lots have lost this ability to induce the pyrogen. The implication of these data is that methionyl-hGH is not itself a pyrogen-inducer but rather may be contaminated with substances which stimulate human LP production. This is not an unexpected finding since several bacterial products, particularly from gram-negative bacteria, are known activators of monocyte LP synthesis and release.

Subsequent testing of hGH in humans was carried out during a repeat phase I trail using a preparation of hGH which was based on purification procedures used for preparations 316-2-1 and 316-2-2 in Table VII. The resultant hGH preparation, labeled 009B1, was tested with cells from six donors and consistently did not induce LP in vitro under the same conditions described. The results of these repeat trials indicated no pain, fever, or other signs of inflammation. Thus, the LP assay was effective in predicting human responses to an agent which had previously been highly inflammatory and pyrogenic.

The invention now being fully described, it will be apparent to one or ordinary skill in the art that many changes and modifications can be made thereto without departing from the spirit or scope of the invention as set forth herein.

What is claimed as new and desired to be secured by Letters Patent of the United States is:

1. A method for determining the pyrogenicity of a substance, comprising the step of:
incubating said substance in the presence of a cell mixture for at least 46 hours at 35° to 39° C., wherein said cell mixture comprises human lymphocytes and human monocytes with a cell ratio of lymphocytes to monocytes of at least 2:1 and a composition with respect to the total of all cells present comprising at least 15% monocytes and no more than 10% granulocytes and wherein said cells have a cell contact ratio of from 0.0 to 0.75.

2. The method of claim 1, wherein said cell mixture is present in a culture medium at a cell concentration of from $1 \times 10^5$ to $2.5 \times 10^7$ total lymphocyte and monocyte cells per milliliter of medium.

3. The method of claim 1, wherein said cell concentration is from $2.5 \times 10^6$ to $1 \times 10^7$ total lymphocyte and monocyte cells per milliliter.

4. The method of claim 1, wherein said cell concentration is about $5 \times 10^6$ total lymphocyte and monocyte cells per milliliter.

5. The method of claim 1, wherein said cell contact ratio is from 0.10 to 3.0 unit contact ratio.

6. The method of claim 1, wherein said cell contact ratio is from 0.33 to 2.0 unit contact ratio.

7. The method of claim 1, wherein said cell contact ratio is about 1 unit contact ratio.

8. The method of claim 1, wherein said composition comprises at least 20% monocytes.

9. The method of claim 8, wherein said composition comprises about 25% monocytes.

10. The method of claim 1, wherein said composition comprises no more than 8% granulocytes.

11. The method of claim 10, wherein said composition comprises no more than 5% granulocytes.

12. The method of claim 1, wherein said incubating occurs in a flat-bottomed container.

13. The method of claim 12, wherein said flat-bottomed container has a bottom surface area of from 1 to 25 square centimeters per milliliter of cell mixture.

14. The method of claim 13, wherein said surface area is from 2 to 10 square centimeters per milliliter of cell mixture.

15. The method of claim 14, wherein said surface area is about 5 square centimeters per milliliter of cell mixture.

16. The method of claim 1, wherein said substance is a pharmaceutical composition proposed for parenteral use in a human at a dosage measured as a number of milligrams of substance per kilogram of body weight and the amount of said substance incubated in the presence of said cell mixture is from 0.1 to 10 times said dosage number per $10^6$ mononuclear cells in said cell mixture.

17. The method of claim 16, wherein said amount is 0.5 to 2 times said dosage number.

18. The method of claim 17, wherein said amount equals said number.

19. The method of claim 1, wherein said cell mixture is obtained from blood taken from an adult human.

20. The method of claim 19, wherein said adult human is at least 18 and no more than 65 years of age.

21. The method of claim 20, wherein said adult human is no more than 55 years of age.

22. The method of claim 20, wherein said adult human is no more than 35 years of age.

23. The method of claim 19, wherein said adult human has not been diagnosed to have diabetes, hepatitis, or an autoimmue disorder.

24. The method of claim 23, wherein said human further has not been diagnosed to have influenza, pharyngitis, or an upper respiratory infection within 14 days immediately preceding a day on which blood is taken.

25. The method of claim 24, wherein said human has taken no medication selected from the group consisting of megavitamins, birth control pills, anti-depressants, narcotics, anti-hypertensives, and anti-anxiety preparations once weekly or more frequently during a period of one year immediately preceding said day.

26. The method of claim 25, wherein said human has not used a psychotomimetic drug more than once a month during a period of one year immediately preceding said day.

27. The method of claim 25, wherein no aspirin, antihistamine, analgesic, or anti-inflammatory drug has been administered to said human within 5 days immediately preceding said day.

28. The method of claim 1, wherein said method comprises the additional step of assaying a supernatant of said cell mixture obtained after said incubating for the presence of human leukocytic pyrogen.

29. The method of claim 28, wherein said assaying comprises the step of measuring febrile response in an animal to an injection of said supernatant.

30. The method of claim 29, wherein said animal is a rabbit.

31. The method of claim 29 or 30, wherein said supernatant is derived from $5 \times 10^4$ to $5 \times 10^6$ monocytes per kilogram of rabbit body weight.

32. The method of claim 31, wherein said supernatant is derived from $5 \times 10^5$ monocytes per kilogram.

33. The method of claims 28, wherein said assaying is by an immunoassay.

34. The method of claim 33 wherein said immunoassay is a radioimmunoassay.

35. The method of claim 1, wherein said incubating is for 46 to 168 hours.

36. The method of claim 35, wherein said incubating is for 46 to 50 hours.

37. The method of claim 1, wherein said incubating is at 37° C.±0.5° C.

38. The method of claim 1, wherein said incubating is in the presence of humidified air.

39. The method of claim 38, wherein said humidified air contains 5%±% $CO_2$.

40. The method of claim 1, wherein said cell mixture is present in a culture medium comprising water, NaCl, KCl, $NaH_2PO_4$, $CaCl_2$, $MgSO_4$, $NaHCO_3$, phenol red, glucose, L-glutamine, streptomycin, Penicillin G, and HEPES buffer.

41. The method of claim 40, wherein said medium is Earl's Balanced Salt Solution containing 2mM L-glutamine, 100 mg/ml streptomycin, 100 units/ml Penicillin G, and 0.01 M HEPES buffer.

42. A method for determining the pyrogenicity of a substance, comprising the step of incubating said substance in the presence of a cell mixture for 46 to 50 hours at 37±0.5° C. in a flat-bottomed container, wherein said cell mixture comprises human lymphocytes and human monocytes with a cell ratio of lymphocytes to monocytes of at least 2:1 and a composition with respect to the total of all cells present comprising at least 15% monocytes and no more than 10% granulocytes in a liquid culture medium at a cell concentration of about $5 \times 10^6$ total lymphocyte and monocyte cells per milliliter and wherein said flat-bottomed container has a bottom surface area of about 5 square centimeters per milliliter of cell mixture.

43. The method of claim 42, wherein said method comprises the additional step of assaying a supernatant of said cell mixture for the presence of human leukocytic pyrogen after said incubating.

44. The method of claim 43, wherein said assaying comprising the step of measuring febrile response in a rabbit to an injection of said supernatant wherein said supernatant is derived from about $5 \times 10^5$ monocytes per kilogram of rabbit body weight.

45. The method of claim 43, wherein said assaying is by an immunoassay.

46. The method of claim 44 or 45, wherein said cell mixture is obtained from the blood of an adult human inclusively between the ages of 18 and 65 who has not been diagnosed to have diabetes, hepatitis, or an autoimmune disorder; who has not been diagnosed to have influenza, pharyngitis, or an upper respiratory infection within 14 days immediately preceding a day on which blood is taken; who has taken no medicine selected from the group consisting of megavitamins, birth-control pills, anti-depressants, narcotics, anti-hypertensives, and anti-anxiety preparations once weekly or more frequently during a period of one year immediately preceding said day; who has not used a psychotomimetic drug more than once a month during said year; and who has taken no aspirin, antihistamine, analgesic, or anti-inflammatory drug within 5 days immediately preceding said day.

47. The method of claim 44 or 45, wherein said substance is a pharmaceutical composition prepared for parenteral use in a human at a dosage measured as a number of milligrams of substance per kilogram of body weight and the amount of said substance incubated in the presence of said cell mixture equals said number of milligrams per $10^6$ mononuclear cells in said cell mixture.

48. The method of claim 46, wherein said substance is a pharmaceutical composition prepared for parenteral use in a human at a dosage measured as a number of milligrams of substance per kilogram of body weight and the amount of said substance incubated in the presence of said cell mixture equals said number of milligrams per $10^6$ mononuclear cells in said cell mixture.

* * * * *